United States Patent
Rebours (10) Patent No.: US 7,967,783 B2
(45) Date of Patent: Jun. 28, 2011

(54) AUTOMATIC RELAY PUMP SYSTEM AND METHOD

(75) Inventor: Pierre Rebours, Hilaire de Cote (FR)

(73) Assignee: CareFusion 303, Inc., San Diego, CA (US)

( * ) Notice: Subject to any disclaimer, the term of this patent is extended or adjusted under 35 U.S.C. 154(b) by 105 days.

(21) Appl. No.: 12/037,314

(22) Filed: Feb. 26, 2008

(65) Prior Publication Data

US 2008/0269678 A1    Oct. 30, 2008

Related U.S. Application Data

(60) Provisional application No. 60/891,671, filed on Feb. 26, 2007.

(51) Int. Cl.
*A61M 1/00* (2006.01)

(52) U.S. Cl. ........... 604/121; 604/67; 604/118; 604/152

(58) Field of Classification Search ............. 604/65–67, 604/890.1–892.1, 151–155, 118, 121, 122, 604/123, 126
See application file for complete search history.

(56) References Cited

U.S. PATENT DOCUMENTS

| | | | |
|---|---|---|---|
| 4,828,545 A | 5/1989 | Epstein et al. | |
| 6,520,930 B2 * | 2/2003 | Critchlow et al. | 604/67 |
| 6,712,786 B2 * | 3/2004 | Azzolini | 604/80 |
| 2001/0023345 A1 | 9/2001 | Wolff et al. | |
| 2003/0055375 A1 * | 3/2003 | Holst et al. | 604/67 |
| 2004/0010229 A1 * | 1/2004 | Houde et al. | 604/151 |

FOREIGN PATENT DOCUMENTS

| | | |
|---|---|---|
| DE | 19859811 A1 | 6/2000 |
| DE | 19900936 A1 | 7/2000 |
| EP | 1611909 A1 | 1/2006 |

OTHER PUBLICATIONS

International Search Report and Written Opinion PCT/US2008/002490 mailed Jul. 3, 2008.

* cited by examiner

*Primary Examiner* — Nicholas D Lucchesi
*Assistant Examiner* — Leah Stohr
(74) *Attorney, Agent, or Firm* — McDermott Will & Emery LLP (57) ABSTRACT

An automatic pump relay system includes controllers coupled to drivers for sequentially discharging fluid from a plurality of medication containers into a coupler having a reflux barrier from which fluid is administered to a patient. The internal fluid pressure of the coupler is determined by a pressure sensing device or devices that provide signals to the controllers that, based at least on the sensor signals, cause the drivers to operate in reverse and forward directions so as to rapidly decrease and raise the fluid pressure within the coupler during a relay from an empty syringe to a filled syringe, thereby avoiding bolus formation and an interruption in infusion therapy. Independently operable syringes pumps are contemplated to be connected in relay fashion to form a modular system. An associated method is also disclosed wherein a fluid administration pressure is stored for use as a reference during a syringe changeover.

11 Claims, 7 Drawing Sheets

AUTOMATIC RELAY PUMP SYSTEM AND METHOD

BACKGROUND OF THE INVENTION

The invention relates generally to common control over multiple medical pumps and more particularly, to a system and method for controlling multiple pumps to form a pump relay system.

Continuity in administering medical fluids through intravenous ("IV") infusion is desirable in many situations, such as when certain anesthetic medications are being administered or when short-acting medications are being administered to hemodynamically unstable patients. Uninterrupted administration of medication can be achieved for long periods of time by dispensing medication from large medication containers at very low infusion rates. However, such a method is not possible in cases when a needed medication is supplied only in small containers and in cases when a needed medication has a short contextual half life.

Relay systems comprising multiple medication pumps running sequentially to provide continuous infusion therapy are known in the art. Automated relay systems that automatically begin the operation of a second pump upon ceasing the operation of a first pump without the need for manual initiation of that second pump have provided an advantage to medical personnel. However, maintaining continuity in prior relay systems is difficult when they are transported with patients from one location to another. In situations when a syringe has low friction resistance, an unexpected bolus may be injected to the patient when the syringe pump is momentarily raised above the patient during transport. Also, infusion may undesirably be interrupted when the syringe pump is subsequently lowered to the same level of the patient. Such changes in medication administration can have adverse effects in situations that require the very precise and accurate infusion of medication.

In addition to being sensitive to transportation, prior relay systems require much attention from medical staff to ensure that a changeover from an empty syringe to a filled syringe occurs without introducing an unexpected bolus or an interruption in medication administration. Replacement of an empty syringe with a filled syringe often requires carefully purging air from fluid tubing and other fluid communication channels. Purging and other activities required to ensure a successful changeover often require medical staff members to momentarily focus their attention on medical equipment rather than on the patient. However, patients that need continuous medication administration are often in critical or unstable condition and should be monitored very closely. Thus, it is desirable to reduce and simplify the activities that are required to ensure a successful changeover.

Hence those skilled in the art have recognized a need for a more efficient and automated relay pump system and method for sequentially operating on multiple separate medical fluid containers to achieve substantially continuous flow of fluid through a tube from those containers. Those skilled in the art have also recognized a need for a relay system and method that avoids the creation of a bolus of fluid during the relay operation and which is less sensitive to transportation and is less sensitive to frictional and mechanical variations of syringes. The present invention fulfills these and other needs.

SUMMARY OF THE INVENTION

Briefly and in general terms, the present invention is directed to an automatic relay pump system and method that monitors the pressure in a fluid line or lines upstream of a reflux barrier and which performs a relay operation between multiple pumps while maintaining pressure control in a fluid tube. In particular, there is provided a continuous pump relay system comprising a plurality of drivers configured to discharge fluid from a plurality of medication containers, a fluid communication device including a plurality of fluid inputs, each one of the fluid inputs configured to receive fluid from a medication container, and a fluid output having a reflux barrier configured to allow fluid in the fluid communication device to flow through the reflux barrier, a pressure sensing device configured to generate sensor signals representative of fluid pressure at one or more locations within the fluid communication device, and a controller coupled to the driver and the pressure sensing device, the controller configured to operate the driver based at least on the sensor signals from the pressure sensing device.

In other aspects, the fluid communication device comprises extension tubes having proximal ends and distal ends, the proximal ends each having a valve mechanism configured to open when connected to a medication container and to close when disconnected from a medication container, the distal ends adapted to be joined by a connector to the reflux barrier. The pressure sensing device includes sensors disposed between the proximal ends and the distal ends of the extension tubes.

In other aspects, the controller operates the respective driver in a reverse direction with respect to the first medication container to decrease the pressure within the fluid communication device. After the controller operates the driver in the reverse direction with respect to the first medication container, the controller operates the respective driver in a forward direction with respect to a second medication container to increase the pressure within the fluid communication device to a reference pressure. The controller operates the second driver in the forward direction with respect to the second medication container to raise the pressure within the fluid communication device at a first rate of increase for a fraction of the increase required to reach the reference pressure, and at a second rate of increase, less than the first rate of increase, for the remaining increase required to reach the reference pressure, wherein the reference pressure is a pressure at which fluid flows out of the reflux barrier of the fluid communication device. In another aspect, the reference pressure is a pressure at a time corresponding to an interruption in a pressure increase arising after the driver begins to discharge fluid from the first medication container.

In more detailed aspects in accordance with the invention, the pressure sensing device includes sensors configured to generate sensor signals representative of pressure at a plurality of monitoring locations within the fluid communication device. The reference pressure is a pressure at a time corresponding to an interruption in a pressure increase arising after the driver begins to discharge fluid from the first medication container, the interruption in the pressure increase occurring at two or more of the monitoring locations within the fluid communication device.

In aspects related to a method in accordance with the invention, there is provided a continuous medication infusion relay method comprising discharging fluid contained in a first medication container through a fluid communication device, determining fluid pressure within the fluid communication device, storing a reference pressure at a time corresponding to fluid flow out of the fluid communication device, reducing the fluid pressure within the fluid communication device, increasing the fluid pressure within the fluid communication device to the stored reference pressure, and discharging fluid contained in a second medication container through the fluid communication device.

In more detailed aspects, discharging the fluid contained in the first medication container comprises moving a plunger of a syringe. Discharging the fluid contained in the first medication container comprises peristaltic pumping of the fluid. Determining the fluid pressure comprises measuring a distance between walls of the fluid communication device. Determining the fluid pressure comprises measuring a load exerted on a sensor by a wall of the fluid communication device. Determining the fluid pressure comprises obtaining signals generated by a sensor contacting fluid within the fluid communication device.

In yet other aspects, storing the reference pressure comprises monitoring a pressure increase within the fluid communication device that occurs after fluid begins to be discharged from the first medication container, and storing the reference pressure when there is in interruption in the pressure increase within the fluid communication device. Monitoring the pressure increase within the fluid communication device comprises monitoring the pressure increase at a plurality of monitoring locations within the fluid communication device. Storing the reference pressure comprises storing the reference pressure when an interruption in pressure increase has occurred at two or more of the monitoring locations within the fluid communication device. Reducing fluid pressure within the fluid communication device comprises reversing the operation of a pump associated the first medication container without affecting fluid pressure within an administration tube distal to the fluid communication device. Increasing the fluid pressure within the fluid communication device to the reference pressure comprises operating a pump associated with the second medication container.

In further method aspects, operating the pump associated with the second medication container comprises operating the pump at a first predetermined speed for a fraction of the pressure increase required to reach the reference pressure, and operating the pump at a second predetermined speed, less than the first predetermined, for the remaining pressure increase required to reach the reference pressure. The method further comprises replacing the first medication container with a third medication container without introducing air into the fluid communication device.

In yet further system aspects, there is provided a continuous medical pump relay system comprising a plurality of drivers configured to discharge fluid from a plurality of medication containers, a fluid communication device having a plurality of fluid inputs, each one of the fluid inputs configured to receive fluid from a medication container, and a fluid output including a reflux barrier, the reflux barrier configured to provide resistance to fluid flow out of the fluid communication device and into an administration tube connected to a patient and configured to prevent a decrease in fluid pressure in the fluid communication device from decreasing fluid pressure within the administration tube, a pressure sensing device configured to generate sensor signals representative of fluid pressure at one or more locations within the fluid communication device, and a controller coupled to the driver and the pressure sensing device, the controller configured to operate the driver based at least on the sensor signals from the pressure sensing device such that fluid pressure within the communication device is decreased by running the driver in a reverse direction with respect to a first medication container, where after fluid pressure within the communication device is raised to a reference pressure by running the driver in a forward direction with respect to a second medication container, the reference pressure being a pressure required to overcome the reflux barrier's resistance to fluid flow out of the fluid communication device.

In accordance with yet further detailed aspects, the fluid communication device comprises extension tubes having proximal ends and distal ends, the proximal ends each having a valve mechanism configured to open automatically when connected to a medication container and to close automatically when disconnected from a medication container, the distal ends adapted to be joined to the reflux barrier by a connector. The pressure sensing device includes sensors configured to generate sensor signals representative of pressure at a plurality of monitoring locations within the fluid communication device. The reference pressure is a pressure at a time corresponding to an interruption in a pressure increase arising after the driver begins to discharge fluid from the first medication container, the interruption in the pressure increase occurring at two or more of the monitoring locations within the fluid communication device.

DETAILED DESCRIPTION OF THE PREFERRED EMBODIMENTS

Figure 1:
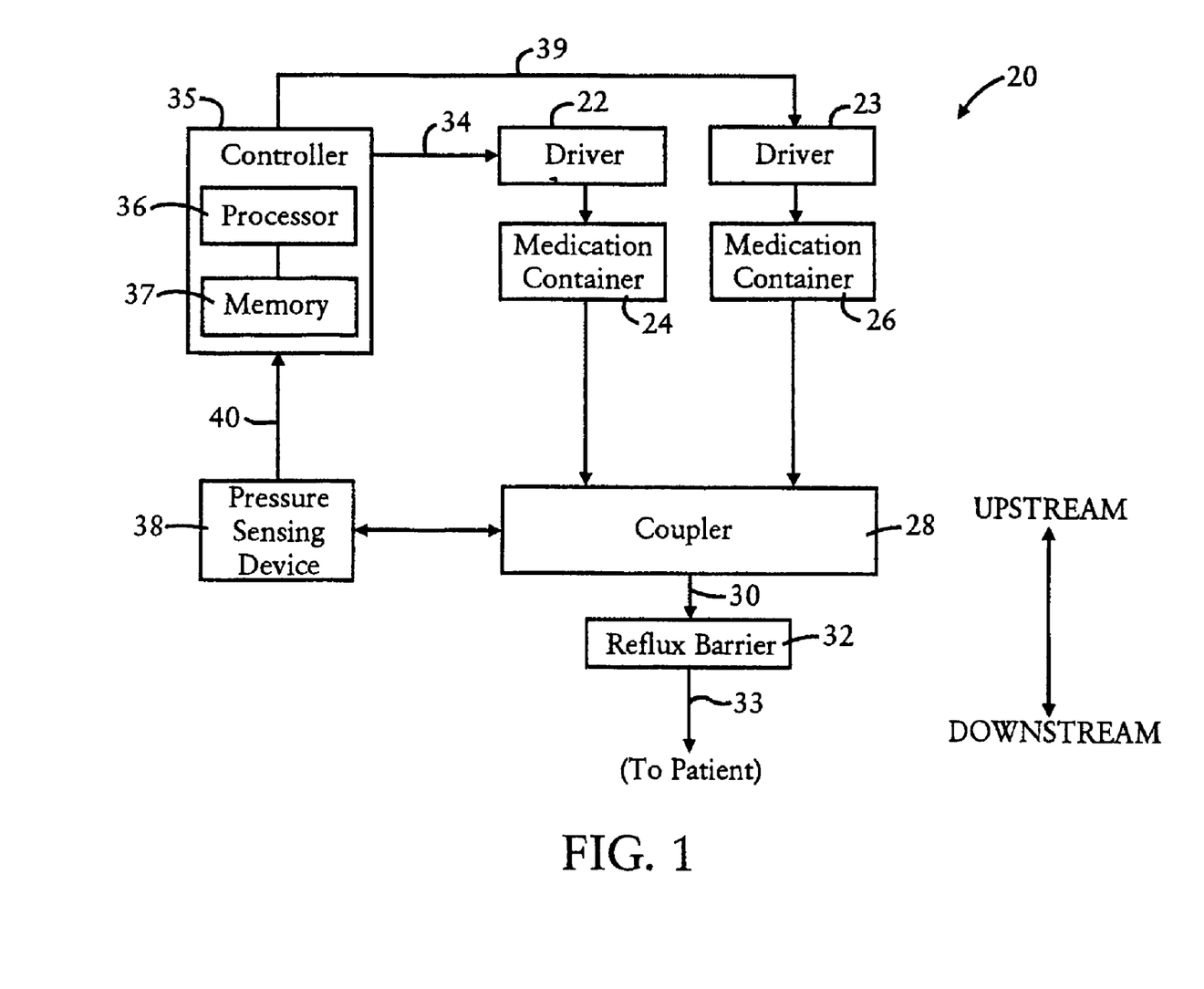
FIG. 1 is a block diagram of an automatic infusion relay system showing a controller providing control signals based at least on signals from a pressure sensing device, the control signals providing instructions to two drivers for discharging fluid from two medication containers both of which are coupled to a fluid communication device, with a reflux barrier located downstream and through which fluid flows.

Referring now in more detail to the exemplary drawings, wherein like reference numerals designate corresponding or like elements among the several views, there is shown in FIG. 1 a block diagram of an automatic infusion relay system 20 having a first driver 22 and a second driver 23 for driving fluid from a plurality of respective medication containers 24 and 26 to a fluid communication device or coupler 28. The medication containers can be syringes, bags, bottles, or other containers or combinations thereof suitable for a fluid intended to be administered to a patient. The coupler may include a flexible or rigid tube, a Y-site, a reservoir, and/or other fluid communication device capable of receiving fluid discharged from the medication containers and providing the received fluid to a different conduit, which in this case is a single conduit. The coupler may also include extension sets comprising a short length of tube and a connector device or devices connected to the containers.

The fluid 30 exits the coupler 28, flows downstream through a fluid reflux barrier 32, and may then continue to flow to a patient through a medical fluid administration set ("administration set") 33 comprising a length of tubing. The reflux barrier performs an anti-siphoning action in that it prevents the siphoning of fluid back into the coupler when fluid pressure in the coupler is relatively low compared to the patient side 33 of the reflux barrier. It therefore functions as a one-way flow valve allowing flow from the upstream to the downstream direction but preventing flow from the downstream to the upstream direction. The drivers 22 and 23 are configured to discharge fluid from each of the medication containers 24 and 26 independently in accordance with control signals 34 and 39 from a controller 35 having a processor 36 with an associated memory device or devices 37. The drivers may be individual pumps or may comprise a single driver device associated with a multi-channel medication pump, or other possible arrangement.

Preferably, fluid from a first medication container 24 is discharged while fluid from a second medication container 26 is held in reserve. When the first medication container is depleted or nearly depleted of fluid, the controller 35 automatically executes a relay function, sending control signals instructing the first driver 22 to cease administration of fluid from the first medication container and the second driver 23 to begin administration of fluid from the second medication container in a closely-timed sequence. A pressure sensing device 38 provides the controller with sensor signals 40 representative of fluid pressure within the coupler 28. The pressure sensing device may include one or more sensors for determining fluid pressure at various locations within the coupler. In any case, the pressure sensing device allows the relay function to be executed such that there is no bolus created and no interruption in fluid administration as will be described in further detail below.

Figure 2:
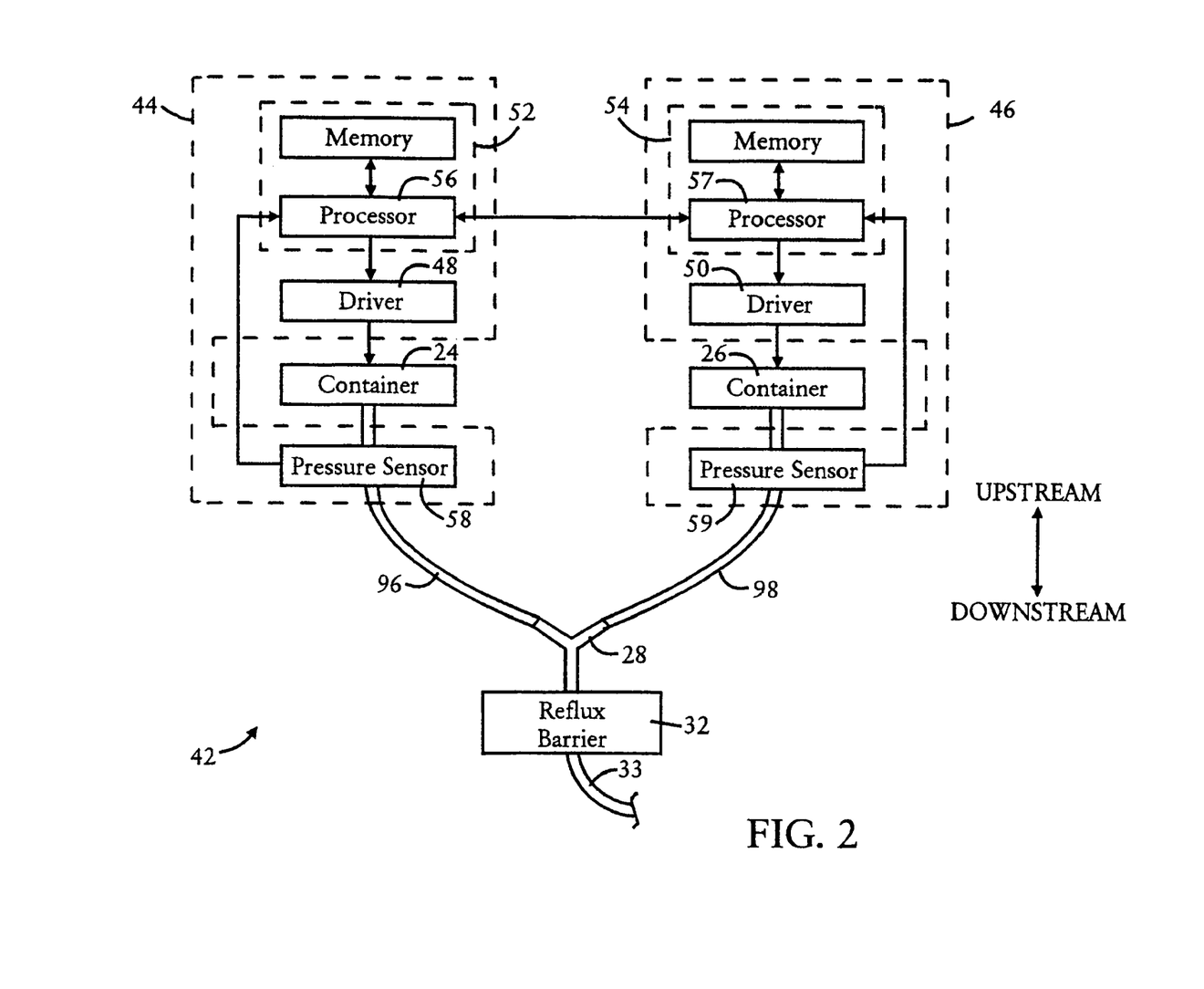
FIG. 2 is a block diagram of an automatic infusion relay system in accordance with aspects of the invention cooperatively operated between two separate pumps each operating on a respective medical fluid container, each pump having a controller including a processor and a memory in this embodiment, with a pressure sensor in each upper infusion line, the system also having a downstream reflux barrier through which fluid flows.

Referring next to FIG. 2, a modular automatic infusion relay system 42 includes two medication pumps 44, 46 that discharge fluid from separate medication containers 24, 26. The medication pumps have separate drivers 48, 50 and controllers 52, 54. Examples of medication pumps, without limitation, include syringe pumps and peristaltic pumps. FIG. 2 also shows the interconnection of the processors 56 and 57 of the controllers of the two relayed pumps. Both pump controllers are configured to the "relay" mode. In the "relay" mode, the processor of each controller retrieves the appropriate instructions from its respective memory 52 and 54 and then interacts with the other "relayed" pump to establish a pump relay system where the relayed pumps sequentially and automatically expel the contents of their respective syringes into the fluid line 33. The modular relay system has the advantage of allowing the medication pumps to be disconnected from each other and used separately for different patients as needed. This versatility and flexibility allows institutions to make use of their equipment inventory in various applications as needed.

In FIG. 2, each pump 44 and 46 has an extension tube set 96 and 98 coupling its container (syringe in this case) 24 and 26 to a Y-site coupler 28 that interconnects the two syringe lines 96 and 98. Pressure in one syringe extension line will equalize with the pressure in the other syringe's extension line because of this interconnection. Downstream of this interconnection of lines is an isolation device, in this case, a reflux barrier 32. The reflux barrier isolates the downstream administration set tube 33 from certain pressure levels that may exist in the syringe extension lines 96 and 98 and prevents the flow of fluid upstream from the administration set tube 33. Because the reflux barrier is essentially a one way valve, it has a cracking pressure that must be met before the reflux barrier will open to permit the flow of fluid through it. In this case it will permit the flow of fluid from the syringes downstream toward the patient but will prevent fluid flow in the opposite direction. Below this cracking pressure, changes of pressure in the extension lines from the syringes will not be communicated downstream past the reflux barrier.

Figure 3:
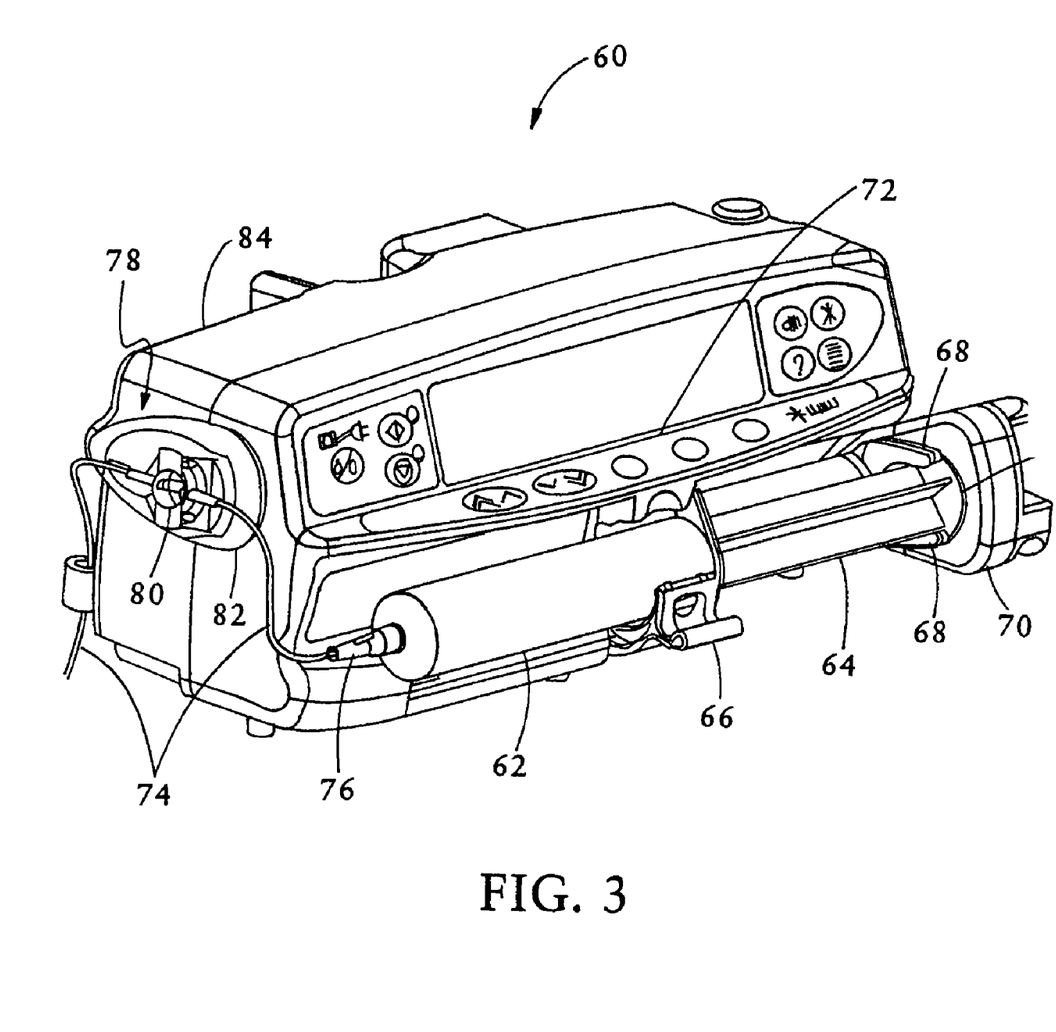
FIG. 3 is a perspective front view of an exemplary syringe pump having mounted thereon a fluid container, in this case a syringe, within which is medical fluid, showing a plunger driver attached to a syringe plunger by plunger grippers for moving the syringe plunger so as to selectively discharge fluid from the syringe into an extension tube that is mounted to a pressure sensor on the housing of the syringe pump, in this embodiment.

FIG. 3 shows an exemplary syringe pump 60, two or more of which may be relayed together to form a modular automatic infusion relay system as shown in FIG. 2 and described above. The syringe pump is configured to dispense fluid from a syringe 62 having a syringe plunger 64. The syringe is locked in place on the syringe pump by a syringe clamp 66. Plunger grippers 68 secure the syringe plunger to a plunger driver 70 that pushes the syringe plunger forward to displace fluid within the syringe in accordance with parameter settings typically provided to the controller (not shown) of the syringe pump by the user through the control panel 72. The plunger grippers prevent the syringe plunger from unexpectedly pulling forward away from the driver, such as what might occur when the syringe pump is raised above a patient and siphoning occurs. The plunger driver may also need to "back off" or pull the syringe plunger rearward to relieve pressure buildup that may be detected, such as for example when there is an occlusion or blockage in an administration tube connected to a patient. "Backing off" is also performed in the operation of the relay system in accordance with aspects of the invention, as will be described below. Fluid that is discharged from the syringe flows into a coupler or fluid communication device, which in this embodiment is a disposable extension tube 74 having a proximal end 76 attached to the tip of the syringe. The extension tube includes an inline pressure disk 80 that provides a more efficient interface to a pressure sensor 78 comprising a pressure transducer 82 mounted on the housing 84 of the syringe pump. The pressure disk is firmly mounted to the pressure transducer to provide an accurate measurement of the pressure of the medical fluid within the extension set 74.

Syringe pumps such as that shown in FIG. 3 are available from the ALARIS Products division of Cardinal Health under the brand Alaris® syringe pumps.

The pressure sensor 78 provides feedback in terms of fluid pressure downstream from the syringe 62, which allows the controller (FIG. 2) to automatically compensate for changes in the elevation of the syringe pump 60 relative to the patient and for frictional and other mechanical variations from one syringe to the next. Measurement of fluid pressure within infusion lines is well known in the art and will not be described in further detail here. It will be appreciated by persons of ordinary skill in the art that a variety of approaches may be employed to indirectly or directly determine fluid pressure within the extension tube 74. One approach is to take readings from a gage or sensor contacting the fluid within the extension tube. Preferably, the approach employed introduces no significant resistance to fluid flow within the extension tube, such as for example, measuring a distance between movable walls of the extension tube, measuring a force exerted by a movable wall of the extension tube, and measuring strain on a wall of the extension tube.

Figure 4:
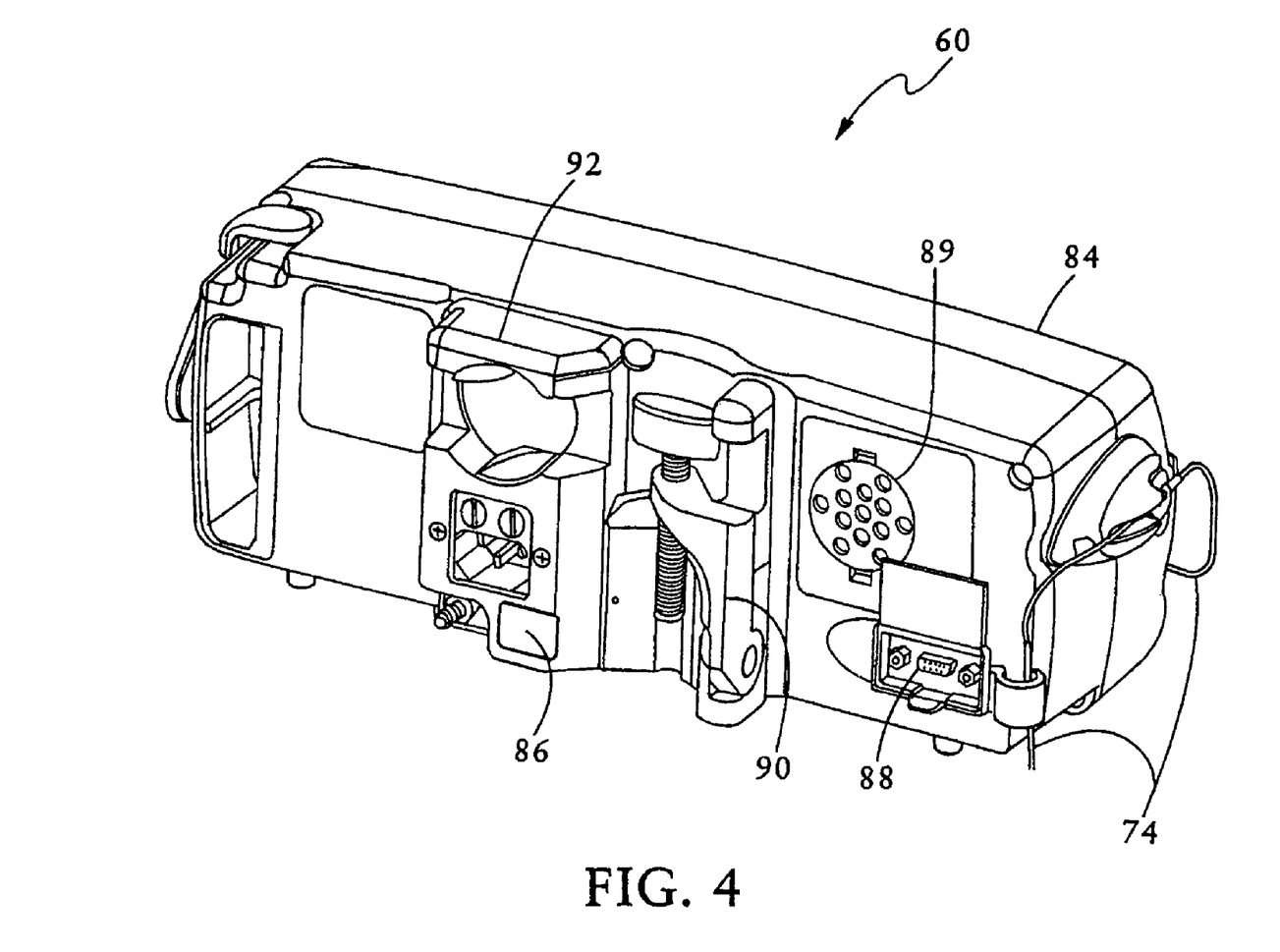
FIG. 4 is a perspective rear view of the syringe pump of FIG. 3 showing an infrared communications port and RS232 serial interface connector, either of which may be used to communicate with a communications network, or another syringe pump, other controller or processor, or other device, and a speaker for audibly indicating changes in infusion status and pump conditions.

FIG. 4 shows the rear of the syringe pump 60 of FIG. 3 where there is an infrared communication port 86 and an RS232 serial interface connector 88, either of which may be used to transmit and receive data, such as control signals and pressure readings, to and from another syringe pump in a modular automatic infusion relay system or processor, or network, or other device. Either or both of the infrared communication port and the RS232 serial interface connector may also be used to receive drug library information and to connect the syringe pump to a hospital information system. There is also a speaker 89 on the housing 84 for transmitting an audible alarm, such as when an occlusion is detected or when fluid in the syringe 62 (FIG. 3) is nearly depleted or completely depleted. The rear of the syringe pump also includes a folding clamp 90 for attaching the pump to a vertical pole along with other pumps and a cam lock 92 for attaching the pump to a horizontal mounting bar.

Figure 5:
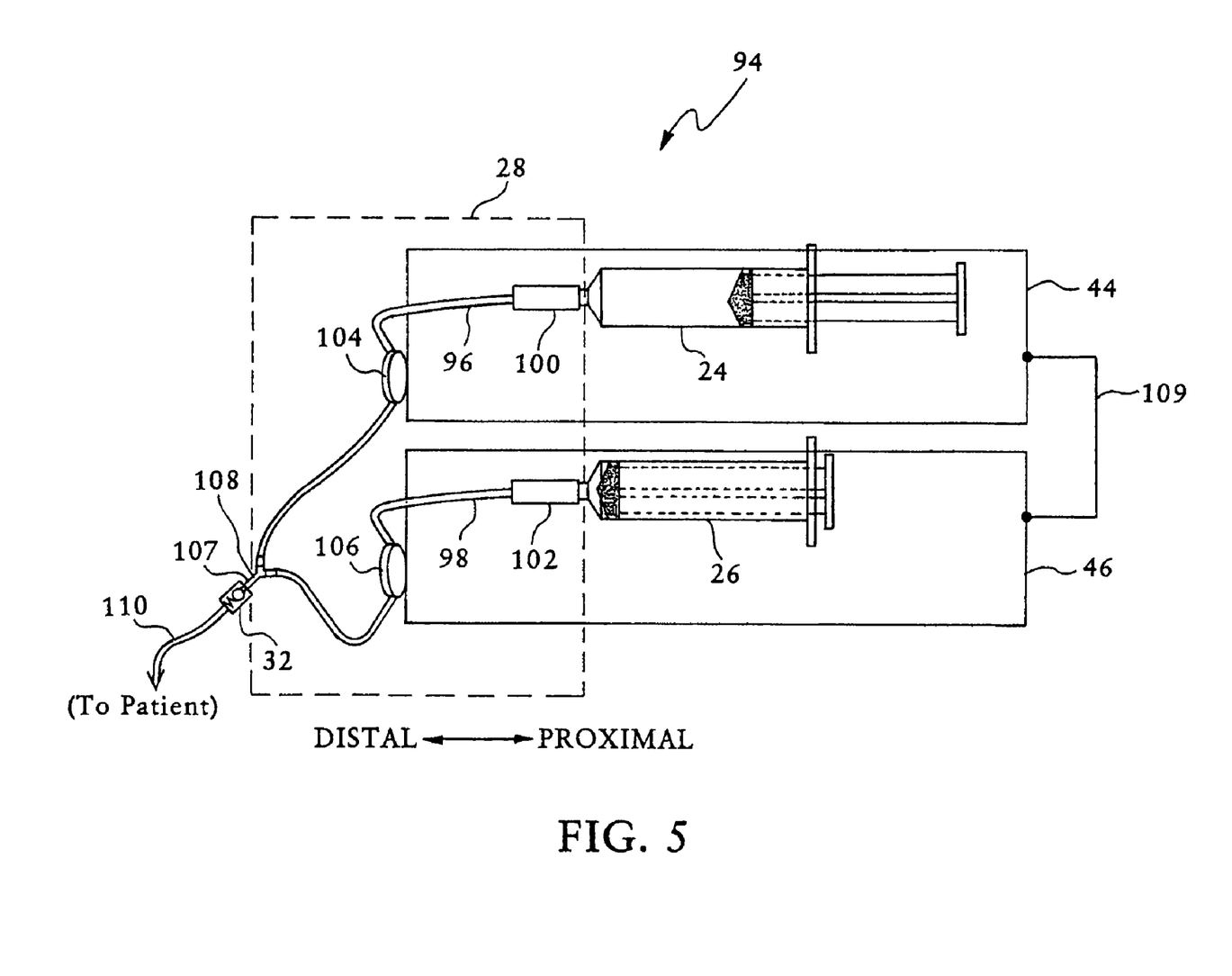
FIG. 5 is a simplified diagram of a modular automatic infusion relay system operating with two self-contained, independently operable syringe pumps selectively connected in relay fashion by means of a fluid communication device with valve mechanisms for connecting syringes to extension tubes attached to separate pressure sensors, the fluid communication device comprising a Y-connector having an output connected to a downstream reflux barrier such as a one-way check valve, the output of which is connected to the tube of an administration set, the system further including a wired or wireless communication link between the two syringe pumps to effect relay control over the two pumps.

In FIG. 5 there is shown a simplified diagram of two syringe pumps 44 and 46 connected in a relay arrangement so as to form a modular infusion relay system 94. An example of a suitable syringe pump includes, but is not limited to, the syringe pump shown in FIGS. 3 and 4. The system includes a first syringe pump 44 and a second syringe pump 46 holding a first syringe 24 and a second syringe 26, respectively. Fluid that is discharged from the syringes flows through a fluid communication device 28 comprising respective extension tubes 96 and 98 having valve mechanisms 100 and 102 at their proximal ends.

The valve mechanisms 100 and 102 are configured to open automatically when connected to a syringe and to close automatically when disconnected from a syringe. When the valve mechanisms are closed, fluid is prevented from flowing through them regardless of internal fluid pressure, thereby preventing fluid leakage from the extension tubes 96 and 98 and air infiltration into the extension tubes 96 and 98 when empty syringes are replaced with filled syringes. Preferably, the valve mechanisms are also configured such that no bolus or pressure buildup develops when a filled syringe is attached to the valve mechanism, such as described in U.S. Pat. No. 6,706,022 to Leinsing, et al., which is incorporated herein by reference. A non-exclusive example of a suitable valve mechanism is the SmartSite® Plus Needle-Free Valve (ALARIS Medical Products division of Cardinal Health, San Diego, Calif.).

The extension tubes 96 and 98 pass through separate pressure sensors 104 and 106 on the syringe pumps and are joined together by a Y-connector 108. Multiple Y-connectors or other types of connectors, such as for example, double Y-connectors, may be used to accommodate three or more syringe pumps in more complex relay systems. The redundancy provided by the two pressure sensors adds to the reliability of the system. Multiple pressure sensors also increase the accuracy of the system since there is now redundancy of sensors to make it more likely that if a sensor becomes inaccurate or inoperative, there will be another sensor that will function correctly. Optionally, pressure readings are shared between the two infusion pumps through a wired or wireless communication link 109. Fluid flows from a fluid output 107 of the Y-connector through a reflux barrier 32 and into the tube 110 of a fluid administration set, the distal end of which may be connected to a patient receiving infusion therapy. The reflux barrier 32 is configured to prevent siphoning or backflow of fluid from the administration tube 110 into the Y-connector 108, such as when fluid pressure in the extension tubes is lower than the pressure in the administration tube. Although the reflux barrier is illustrated symbolically as a spring-loaded ball valve, it will be immediately appreciated by persons of ordinary skill in the art that the reflux barrier may have other suitable configurations. The reflux barrier functions as a one-way valve.

Figure 6:
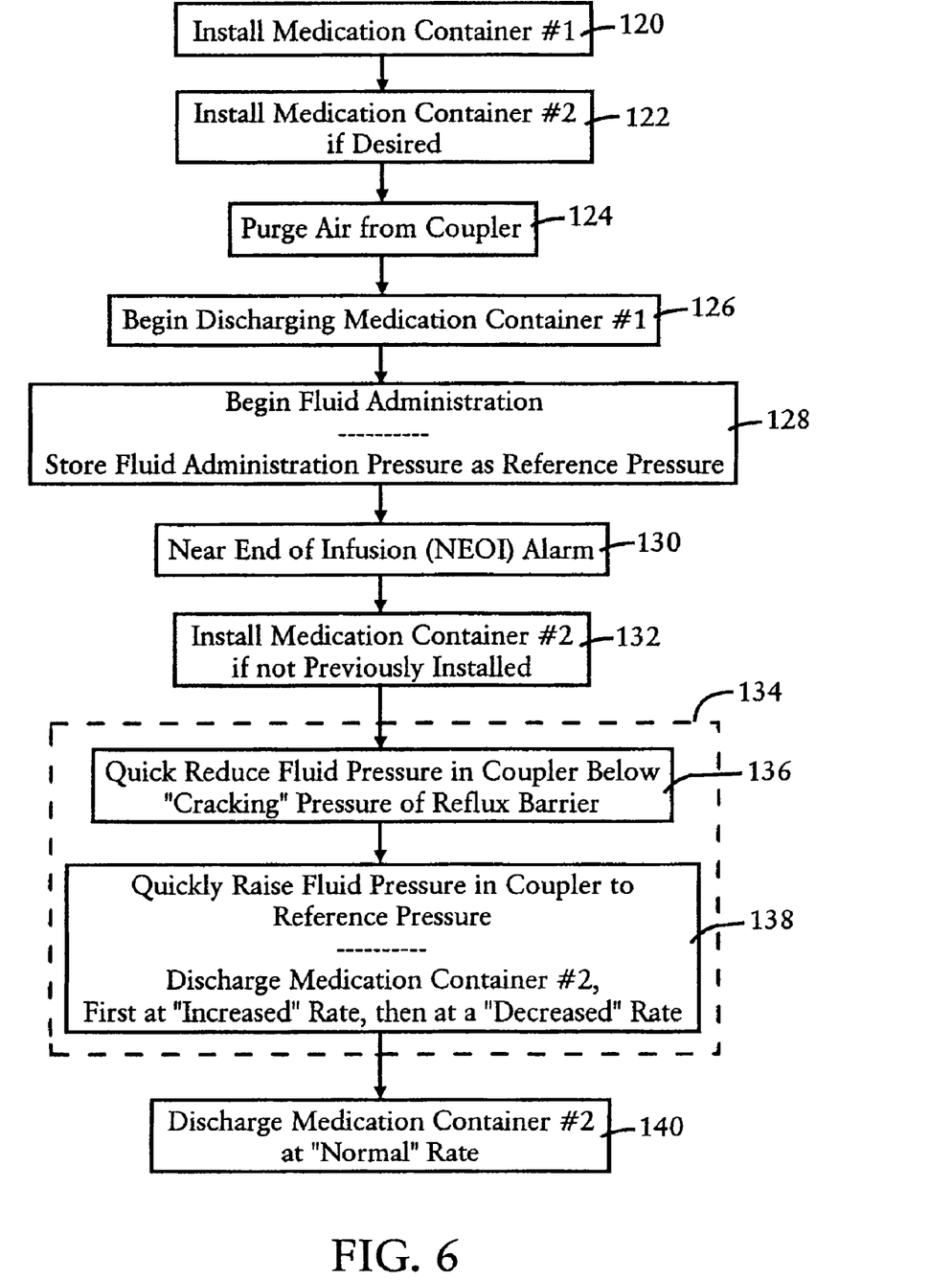
FIG. 6 is a flow diagram illustrating an exemplary method of providing an automatic pump relay method in accordance with aspects of the invention by storing a fluid administration pressure and executing an automatic relay from an empty medication container to a filled medication container, during which the pressure within a fluid communication device is quickly reduced by the depleted container and is then restored to the previously stored administration pressure by the filled container in accordance with aspects of the invention.

FIG. 6 shows an exemplary method of providing an automatic pump relay in accordance with aspects of the invention. Although this method will be described with reference to elements of the modular relay system 94 of FIG. 5, the method is equally applicable to other relay system configurations. A first syringe is installed in the first syringe pump and connected to the first extension tube at block 120 of the method. A second syringe, which is to be discharged after the first syringe, is installed and connected at block 122. In some cases where the efficacy of the fluid decreases rapidly over time, it may be desirable to install the second syringe at a later time. Next, at block 124, air is purged from the administration set including the valve mechanisms, tubes, Y-connector, and reflux barrier using fluid intended to be administered. The first syringe pump is activated at block 126 to begin discharging fluid from the first syringe into the coupler. Initial resistance from the reflux barrier causes fluid pressure to increase within the extension tubes. The pressure increase is interrupted when the initial resistance of the reflux barrier is overcome by the pressure buildup and the reflux barrier reaches its cracking pressure, allowing fluid to flow through the reflux barrier and into the administration tube onto the patient. At about the time of the interruption in pressure increase, the controller stores a pressure reading ("cracking pressure") based at least on pressure sensor signals from the pressure sensors at block 128. Alternatively, the controller may store a pressure reading after pressure readings have further stabilized a short time after the interruption of pressure increase. In any case, the pressure reading is stored by the controller as a reference pressure for use during a subsequent relay function at block 134 as described further below.

When the system is configured with multiple pressure sensors, such as shown in FIGS. 2 and 5, the stored reference pressure preferably corresponds to pressure readings at a time when an interruption or change in the pressure increase has occurred in all pressure sensors. For example, a first pressure sensor may indicate an interruption in pressure increase within a first extension tube while a second pressure sensor indicates no interruption in pressure increase within a second extension tube. Subsequently, the second pressure sensor indicates an interruption, at which point, the controllers in each of the infusion pumps store a reference pressure based on pressure readings from their respective pressure sensors. Alternatively, the pressure readings from all pressure sensors may be averaged to monitor the pressure increase and to obtain a more accurate, common reference pressure. Of course, other statistical approaches or algorithms may be applied to pressure readings to obtain an accurate reference pressure that corresponds to fluid administration. For example, an average may be taken of several readings from each of the pressure sensors.

Typically, a near end of infusion ("NEOI") alarm is provided by an infusion pump when a preselected volume of fluid from the syringe has been administered, such as for example ninety percent of the volume of the medication container or when reaching a predetermined period of time before the present container will be empty, such as one-half hour. The NEOI alarm prompts the user to ensure that the system is prepared to relay from a soon-to-be-empty empty syringe to a filled syringe. After the NEOI alarm of the first syringe turns on at block 130, the user installs the second syringe into the second pump and connects it to the second extension tube at block 132 if it was not previously installed and connected at block 122.

As previously mentioned, the controller executes a relay or changeover function at block 134. The relay function may be manually initiated by a user at any desired time or in response to an NEOI alarm indicating "near end of infusion" or at an EOI ("end of infusion") alarm. Alternatively, the changeover function may be initiated automatically if a filled syringe is detected by the system when an NEOI alarm occurs or when an EOI alarm occurs to indicate that the volume of the present syringe has been almost completely discharged or completely discharged. In accordance with aspects of the invention, at the start of the changeover function, the plunger driver of the first syringe pump backs off by momentarily reversing direction and then stops moving, thereby reducing the fluid pressure within both extension tubes at block 136 to a pressure below the cracking pressure of the reflux barrier. The reflux barrier prevents the reduction in pressure in the extension tubes from being communicated to the administration set, which may otherwise withdraw fluid from the patient into the administration set.

This reduction in fluid pressure in the extension tubes and the isolation provided by the reflux barrier prevent a bolus from being communicated to the patient at block 138, wherein the plunger driver of the second syringe pump automatically begins to run forward to quickly raise the fluid pressure in the extension tubes to a pressure at or above the cracking pressure or other stored reference pressure and preferably to equal the pressure established by the first syringe before being depleted. A situation may arise in which the plunger of the second syringe fails to advance immediately due to static friction when pushed by the plunger driver of the second syringe pump. If a sudden pressure increase forms when the plunger suddenly advances, the sudden pressure increase is absorbed by the reduced fluid pressure within the coupler upstream of the reflux barrier and is not communicated to the administration set that is connected to the patient. The reduced pressure in the extension tubes also has the advantage of helping to accommodate any initial resistance of the plunger. Accordingly, the method and system in accordance with aspects of the invention accommodates variations in friction arising from different types or brands of syringes.

To avoid an interruption in fluid administration, the reduction from one pump and restoration by another pump of fluid pressure in the extension tubes is performed rapidly. The second syringe pump runs in the forward direction automatically either in response to sensing the pressure drop occurring during relay or in response to signals transmitted by the first infusion pump over the communication link (109, see FIG. 5). The second syringe pump runs in the forward direction at an "increased" rate of speed for nine-tenths, or some other fraction, of the lost pressure. The increased rate of speed is significantly higher than the "normal" rate of speed consistent with infusion parameters programmed by the user into the syringe pump. After compensating for nine-tenths of the lost pressure, or some other fraction, the syringe pump runs at a "decreased" or less than normal rate of speed until the fluid pressure in the infusion tubes reaches the reference pressure as indicated by both pressure sensors or another type of pressure sensing arrangement. Approaching the reference pressure at the decreased rate of speed assures that no bolus is created and that administration of fluid to the patient during the changeover remains steady.

After the fluid pressure in the extension tubes reaches the stored reference pressure, the second syringe pump runs at the normal rate of speed at block 140. Thereafter, the user may replace the empty first syringe with a filled third syringe when the NEOI alarm on the second syringe turns on. Because the valve mechanism (100, see FIG. 5) automatically closes when the first syringe is removed, there is no need to purge the extension tubes after the third syringe is connected. The relay function repeats in the manner outlined above such that the second syringe pump backs off and the first syringe pump begins to discharge the third syringe. In this way, administration of fluid may continue indefinitely with successive relays and replacements of empty syringes with filled syringes.

Figure 7:
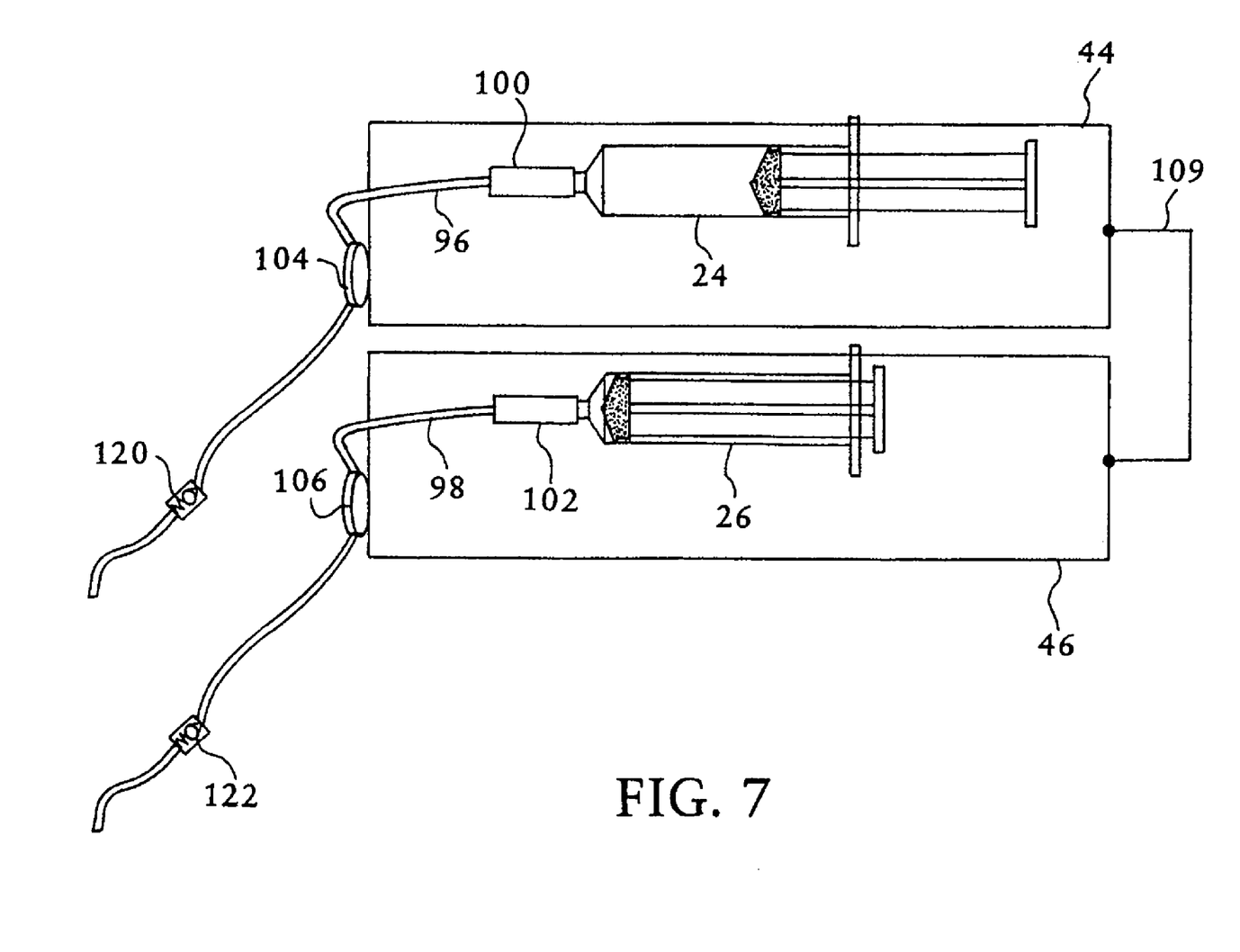
FIG. 7 is a diagram showing two separate syringe pumps, each with its own syringe, coupled in a relay arrangement such that when one syringe is emptied, the other syringe pump will automatically begin pumping the contents of its syringe into the fluid line, each syringe having a separate fluid line with a separate reflux barrier in each line, the lines not being coupled downstream in this embodiment.

Turning now to FIG. 7, there is provided an arrangement of two syringe pumps 44 and 46 very similar to the arrangement in FIG. 5 except that the extension sets 96 and 98 are not coupled together. Instead, they individually are communicating with different portions of the patient (not shown). Each of the administration sets of these pumps has its own reflux barrier 120 and 122. Therefore, the pressure in the extension sets may differ. However, as in FIG. 5, each pump includes a pressure sensor 104 and 106 so that the pressure in the individual extension set may be accurately measured. Additionally, the pumps are placed into communication with each other through a communication line 109 which may be wired or wireless, as discussed above in regard to other embodiments, including FIG. 5. In the case of FIG. 7, the cracking pressure of each reflux barrier would need to be determined and stored by each pump. Otherwise, the operation is essentially the same as with the operation of FIG. 5.

The exemplary systems and method described in accordance with the present invention provides safe, steady, and uninterrupted administration of fluid in cases when it is not feasible to use large volume medication containers to provide long term infusion therapy. One example of such cases is the situation in which a patient must continuously receive medication with a short half-life. Even when the half-life of a medication presents no problem or when large volume medication containers can be used, the present invention allows patient care givers to spend less time changing medication containers and spend more time focused on monitoring the condition of patients.

The function of programming each of the relayed pumps may be synchronized in accordance with aspects of the invention by various means. In one embodiment, programming the rate, VTBI, or other operational parameters, including variable rates, need only be programmed into one of the pumps. That pump may control the others in a master/slave relationship. In another embodiment where a clinical facility desires to be able to remove pumps from a relay arrangement as soon as they are no longer needed, one pump passes off the operational parameters to the next at the time of relay. Then when any pump will no longer be needed for a relay function, it may be removed and used elsewhere. Alternately, programming controls and relay controls may be performed by a separate control unit, a remote processor, a network processor, or other that has a wireless or wired connection to the relayed pumps. Other arrangements are possible and will be apparent to those skilled in the art.

While several particular forms of the invention have been illustrated and described, it will also be apparent that various modifications can be made without departing from the scope of the invention. For example, three or more medication pumps may be connected in relay fashion to provide continuous infusion therapy. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

I claim:

1. A continuous pump relay system comprising:
   at least first and second drivers having forward and reverse directions, wherein the drivers are configured to discharge fluid from at least first and second medication containers, respectively, when operating in the forward direction;
   a fluid communication device including at least first and second fluid inputs configured to receive fluid from the first and second medication containers, and a fluid output having a reflux barrier configured to allow fluid in the fluid communication device to flow through the reflux barrier;
   at least one pressure sensing device configured to generate sensor signals representative of fluid pressure at one or more locations within the fluid communication device; and
   a controller coupled to the first and second drivers and the pressure sensing device, the controller configured to operate the first and second drivers based at least on the sensor signals so as to changeover the system from delivering fluid from the first medication container at a reference pressure to delivering fluid from the second medication container by operating the first driver in the reverse direction to decrease the fluid pressure and then stopping the first driver, and then operating the second driver in the forward direction at a first rate until the fluid pressure reaches a predetermined fraction of the reference pressure and then at a second rate, less than the first rate, until the fluid pressure reaches the reference pressure without creating a bolus.

2. The system of claim 1 wherein the fluid communication device comprises extension tubes having proximal ends and distal ends, the proximal ends each having a valve mechanism configured to open when connected to a medication container and to close when disconnected from a medication container, the distal ends adapted to be joined by a connector to the reflux barrier.

3. The system of claim 2 wherein the pressure sensing device includes sensors disposed between the proximal ends and the distal ends of the extension tubes.

4. The system of claim 1 wherein the reference pressure is a pressure at which fluid flows out of the reflux barrier of the fluid communication device.

5. The system of claim 4 wherein the reference pressure is a pressure at a time corresponding to an interruption in a pressure increase arising after the driver begins to discharge fluid from the first medication container.

6. The system of claim 1 wherein the pressure sensing device includes sensors configured to generate sensor signals representative of pressure at a plurality of monitoring locations within the fluid communication device.

7. The system of claim 6 wherein the reference pressure is a pressure at a time corresponding to an interruption in a pressure increase arising after the driver begins to discharge fluid from the first medication container, the interruption in the pressure increase occurring at two or more of the monitoring locations within the fluid communication device.

8. A continuous medical pump relay system comprising:
   a plurality of drivers configured to discharge fluid from a plurality of medication containers;
   a fluid communication device having a plurality of fluid inputs, each one of the fluid inputs configured to receive fluid from a medication container, and a fluid output including a reflux barrier, the reflux barrier configured to provide resistance to fluid flow out of the fluid communication device and into an administration tube connected to a patient and configured to prevent a decrease in fluid pressure in the fluid communication device from decreasing fluid pressure within the administration tube;
   a pressure sensing device configured to generate sensor signals representative of fluid pressure at one or more locations within the fluid communication device; and
   a controller coupled to the driver and the pressure sensing device, the controller configured to operate the driver based at least on the sensor signals from the pressure sensing device during a changeover from a first medication container to a second medication container such that fluid pressure within the communication device is decreased by running the driver in a reverse direction with respect to the first medication container, whereafter fluid pressure within the communication device is raised to a reference pressure by running the driver in a forward direction with respect to the second medication container, the reference pressure being a pressure required to overcome the reflux barrier's resistance to fluid flow out of the fluid communication device.

9. The system of claim 8 wherein the fluid communication device comprises extension tubes having proximal ends and distal ends, the proximal ends each having a valve mechanism configured to open automatically when connected to a medication container and to close automatically when disconnected from a medication container, the distal ends adapted to be joined to the reflux barrier by a connector.

10. The system of claim 8 wherein the pressure sensing device includes sensors configured to generate sensor signals representative of pressure at a plurality of monitoring locations within the fluid communication device.

11. The system of claim 10 wherein the reference pressure is a pressure at a time corresponding to an interruption in a pressure increase arising after the driver begins to discharge fluid from the first medication container, the interruption in the pressure increase occurring at two or more of the monitoring locations within the fluid communication device.

* * * * *

UNITED STATES PATENT AND TRADEMARK OFFICE
CERTIFICATE OF CORRECTION

| | | |
|---|---|---|
| PATENT NO. | : 7,967,783 B2 | Page 1 of 1 |
| APPLICATION NO. | : 12/037314 | |
| DATED | : June 28, 2011 | |
| INVENTOR(S) | : Pierre Rebours | |

It is certified that error appears in the above-identified patent and that said Letters Patent is hereby corrected as shown below:

IN THE DRAWINGS:

In Sheet 3, Figure 3:   Reference No. 64 is missing from the syringe plunger

Signed and Sealed this
Sixth Day of December, 2011

David J. Kappos
*Director of the United States Patent and Trademark Office*